(12) United States Patent
Kohler et al.

(10) Patent No.: US 12,390,349 B2
(45) Date of Patent: Aug. 19, 2025

(54) LIGAMENT REVISION SYSTEM

(71) Applicant: Conmed Corporation, Utica, NY (US)

(72) Inventors: Adam Kohler, Iowa City, IA (US); Andrew Kam, Odessa, FL (US); Brian R. Wolf, Iowa City, IA (US); Philip Lahey, Greenville, WI (US); Danielle L. Whitlock, Barcelona (ES)

(73) Assignee: Conmed Corporation, Utica, NY (US)

( * ) Notice: Subject to any disclaimer, the term of this patent is extended or adjusted under 35 U.S.C. 154(b) by 671 days.

(21) Appl. No.: 17/255,030

(22) PCT Filed: Jun. 13, 2019

(86) PCT No.: PCT/US2019/036951
§ 371 (c)(1),
(2) Date: Dec. 22, 2020

(87) PCT Pub. No.: WO2020/005556
PCT Pub. Date: Jan. 2, 2020

(65) Prior Publication Data
US 2021/0267769 A1   Sep. 2, 2021

Related U.S. Application Data

(60) Provisional application No. 62/689,391, filed on Jun. 25, 2018.

(51) Int. Cl.
*A61F 2/46* (2006.01)
*A61B 17/92* (2006.01)
(Continued)

(52) U.S. Cl.
CPC ............ *A61F 2/4601* (2013.01); *A61B 17/92* (2013.01); *A61F 2/28* (2013.01);
(Continued)

(58) Field of Classification Search
CPC ............ A61F 2002/4681; A61F 2/4644; A61F 2/4601; A61F 2/0805; A61B 17/885; A61B 2017/922; A61B 17/3417
See application file for complete search history.

(56) References Cited

U.S. PATENT DOCUMENTS 2,955,530 A * 10/1960 Nilo ........................ G01N 1/286
600/573
5,021,056 A * 6/1991 Hofmann ............. A61B 17/152
606/86 R
(Continued)

FOREIGN PATENT DOCUMENTS

CN     104114113 A     10/2014
JP     H07500027 A     8/1996
(Continued)

OTHER PUBLICATIONS

International Search Report Form PCT/ISA/220, International Application No. PCT/US2019/036951, pp. 1-11, Dated Sep. 27, 2019.
(Continued)

*Primary Examiner* — David W Bates
(74) *Attorney, Agent, or Firm* — Bond, Schoeneck & King, PLLC; Frederick J.M. Price (57) ABSTRACT

A device and system for inserting and impacting bone dowel allografts or bone chips into a bone tunnel. The surgical impacting system includes a surgical tamp having a proximal end and a distal end with an elongated shaft extending therebetween. The surgical tamp has an inner channel extending therethrough from the proximal end to the distal end. The distal end of the surgical tamp can have a distal tip. The surgical tamp may have a handle at the proximal end or a proximal tip at the proximal end. The surgical tamp may also have one or more slots extending through the exterior surface of the elongated shaft and into the inner channel. The surgical tamp can be configured for insertion into a delivery
(Continued)

tube. The delivery tube serves the purpose of containing a bone dowel or bone chips therein for smooth insertion into the joint.

7 Claims, 10 Drawing Sheets

(51) Int. Cl.
*A61F 2/28* (2006.01)
*A61B 17/00* (2006.01)

(52) U.S. Cl.
CPC ............ *A61B 2017/00902* (2013.01); *A61B 2017/922* (2013.01); *A61F 2002/2839* (2013.01)

(56) References Cited

U.S. PATENT DOCUMENTS

| | | | | |
|---|---|---|---|---|
| 5,474,554 A * | 12/1995 | Ku | ............ | A61B 17/92 606/86 R |
| 5,800,437 A * | 9/1998 | Gustilo | ............ | A61B 17/885 606/85 |
| 5,910,172 A * | 6/1999 | Penenberg | ............ | A61F 2/4601 606/86 R |
| 5,919,196 A * | 7/1999 | Bobic | ............ | A61F 2/4618 606/88 |
| 6,142,998 A * | 11/2000 | Smith | ............ | A61F 2/4601 604/218 |
| 6,592,588 B1 * | 7/2003 | Bobic | ............ | A61B 17/1637 606/167 |
| 10,085,783 B2 | 10/2018 | Emery et al. | | |
| 2002/0016633 A1 * | 2/2002 | Lin | ............ | A61F 2/4611 623/17.11 |
| 2003/0097135 A1 * | 5/2003 | Penenberg | ............ | A61F 2/4601 606/86 R |
| 2005/0070898 A1 * | 3/2005 | Jones | ............ | A61F 2/4601 606/53 |
| 2006/0161163 A1 * | 7/2006 | Shino | ............ | A61F 2/08 606/86 R |
| 2007/0156020 A1 * | 7/2007 | Foley | ............ | A61M 29/00 600/104 |
| 2009/0054906 A1 * | 2/2009 | Walthall | ............ | A61F 2/4618 606/108 |
| 2010/0191296 A1 * | 7/2010 | Lyon | ............ | A61B 17/8811 606/86 R |
| 2010/0249930 A1 * | 9/2010 | Myers | ............ | A61B 17/1764 623/13.14 |
| 2011/0125272 A1 * | 5/2011 | Bagga | ............ | A61F 2/4601 623/18.11 |
| 2013/0267961 A1 * | 10/2013 | Mauldin | ............ | A61B 17/68 606/99 |
| 2014/0276471 A1 | 9/2014 | Emery et al. | | |
| 2014/0358188 A1 * | 12/2014 | Larson | ............ | A61B 17/8819 606/86 R |
| 2016/0310197 A1 * | 10/2016 | Black | ............ | A61B 17/17 |
| 2016/0317207 A1 * | 11/2016 | Miller | ............ | A61F 2/4601 |
| 2019/0254727 A1 | 8/2019 | Bolosan | | |
| 2020/0375646 A1 * | 12/2020 | Fein | ............ | A61B 17/921 |

FOREIGN PATENT DOCUMENTS

| | | |
|---|---|---|
| JP | 1998-165413 A2 | 6/1998 |
| JP | 2009-518077 A | 5/2009 |
| WO | 2000033750 A1 | 6/2000 |
| WO | 2002034148 A2 | 5/2002 |
| WO | 2016123583 A1 | 8/2016 |

OTHER PUBLICATIONS

KR Office Action, Application No. 10-2021-7000746, dated Oct. 28, 2022, pp. 3-5.
JP Office Action, Application No. 2020-571815, dated Feb. 14, 2022, pp. 1-15.
AU Examination Report, Application No. 2022241568, dated Dec. 22, 2023, pp. 1-7.
EP Office Action, Application No. 19742096.1, dated Apr. 25, 2024, entire document.
Translated Chinese First Notice of Examination Action, App. No. 201980048589.3, dated Jan. 31, 2024, pp. 1-16.

* cited by examiner

LIGAMENT REVISION SYSTEM

CROSS-REFERENCES TO RELATED APPLICATIONS

This application is a national stage application under 35 U.S.C. 371 based on international patent application PCT/US19/36951 filed on Jun. 13, 2019, which claims priority to U.S. Provisional Patent Application Ser. No. 62/689,391, filed on Jun. 25, 2018.

BACKGROUND OF THE INVENTION

1. Field of the Invention

The present invention is directed generally to a surgical system and, more particularly, to a device and system for inserting and impacting bone dowel allografts or bone chips into a bone tunnel.

2. Description of Related Art

In instances where a failed ligament reconstruction needs to be revised, the bone loss incurred after removing the failed graft or fixation hardware may be too significant to perform the revision in a single stage. Therefore, it is necessary to first address the bone loss before reconstructing the ligament in a second stage. In order to address the bone loss, a bone dowel or bone chips are inserted into the bone tunnel (having the bone loss). After time has passed and the bone has healed, the failed ligament reconstruction can be revised.

Figure 1:
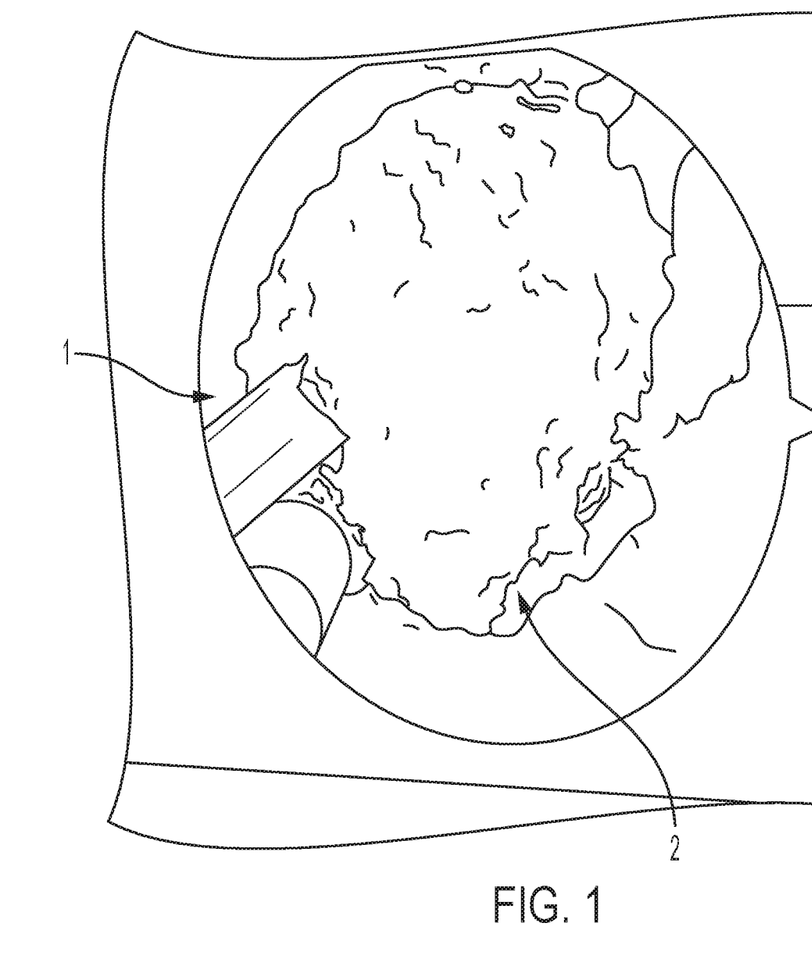
FIG. 1 is an image of a device impacting a bone dowel.
Figure 2:
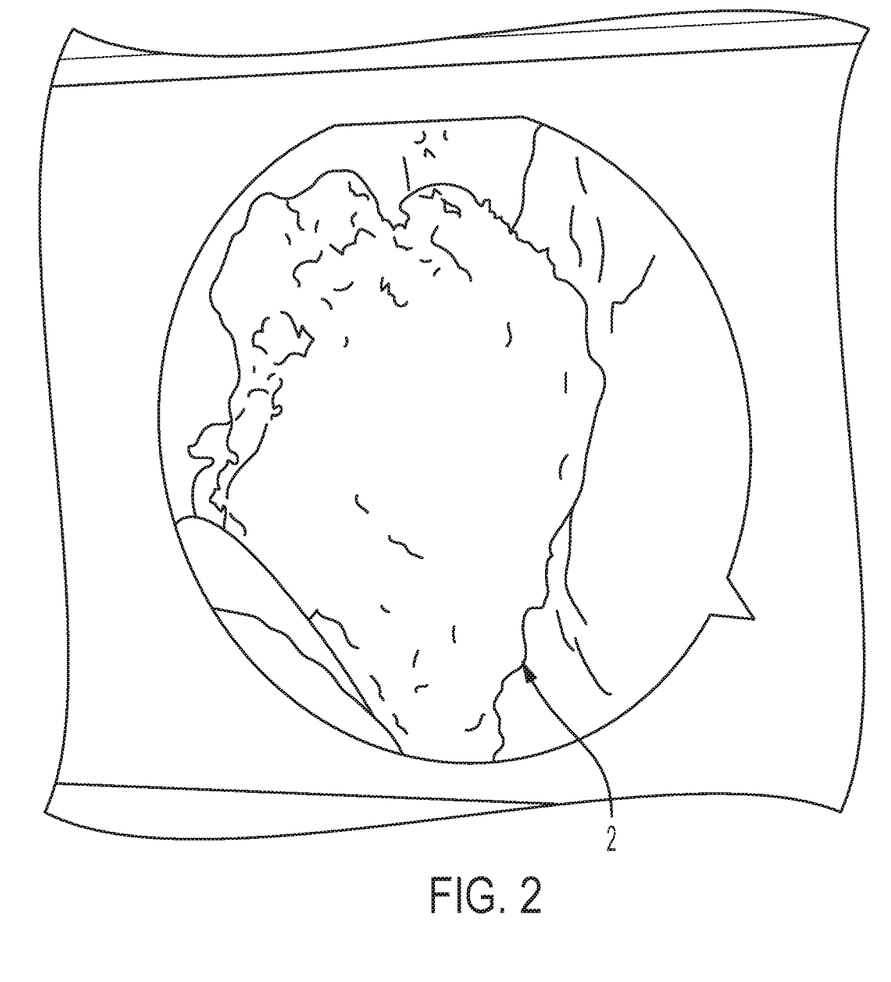
FIG. 2 is an image of a bone dowel inserted into a bone tunnel without a guide pin.

Conventional bone dowels are cannulated to interface with a guide pin which aids in navigating the dowel through the joint into the tunnel. When placed over the guide pin, there is no cannulated tamp or impaction device that can insert the dowel into the tunnel. Surgeons will either use an available device 1 to impact the edges of the bone dowel 2, as shown in FIG. 1, or remove the guide pin and insert the dowel 2 without a guide, as shown in FIG. 2. There are resulting issues/problems with these conventional bone dowels, including the edges of the bone dowel allograft can fracture and crumble during insertion, or without a guide, the bone dowel allograft can fracture and crumble during insertion. Additionally, without a guide, the bone dowel allograft is not properly oriented to be inserted into the tunnel. Another issue is that some surgeons struggle to insert the bone dowel through the skin incision and guide it past the knee structures to the femoral tunnel.

Therefore, there is a need for a device and system for inserting and impacting bone dowels and bone chips into a bone tunnel without the associated problems/issues noted above.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a device and system for inserting and impacting bone dowels and bone chips into a bone tunnel. According to one aspect, the present invention is a surgical impacting system. The system includes a surgical tamp having a proximal end and a distal end with an elongated shaft extending therebetween. The system includes a handle at the proximal end and a cylindrical distal tip at the distal end. The system additionally has an inner channel extending at least partially through the elongated shaft from the proximal end to the distal end.

According to another aspect, the system includes a surgical tamp having a proximal end and a distal end with an elongated shaft extending therebetween. The system also includes a cylindrical proximal tip at the proximal end and a cylindrical distal tip at the distal end. The system additionally has an inner channel extending at least partially through from the proximal end to the distal end.

According to yet another aspect, the present invention is a method for inserting an object into a bone tunnel. The method includes the steps of: (i) providing a surgical tamp having a proximal end and a distal end with an elongated shaft extending therebetween, a cylindrical distal tip at the distal end, and an inner channel extending at least partially through the elongated shaft from the proximal end to the distal end; (ii) inserting an object into the inner channel at the proximal end of the surgical tamp; and (iii) advancing the object within the inner channel to the distal tip of the surgical tamp.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 3:
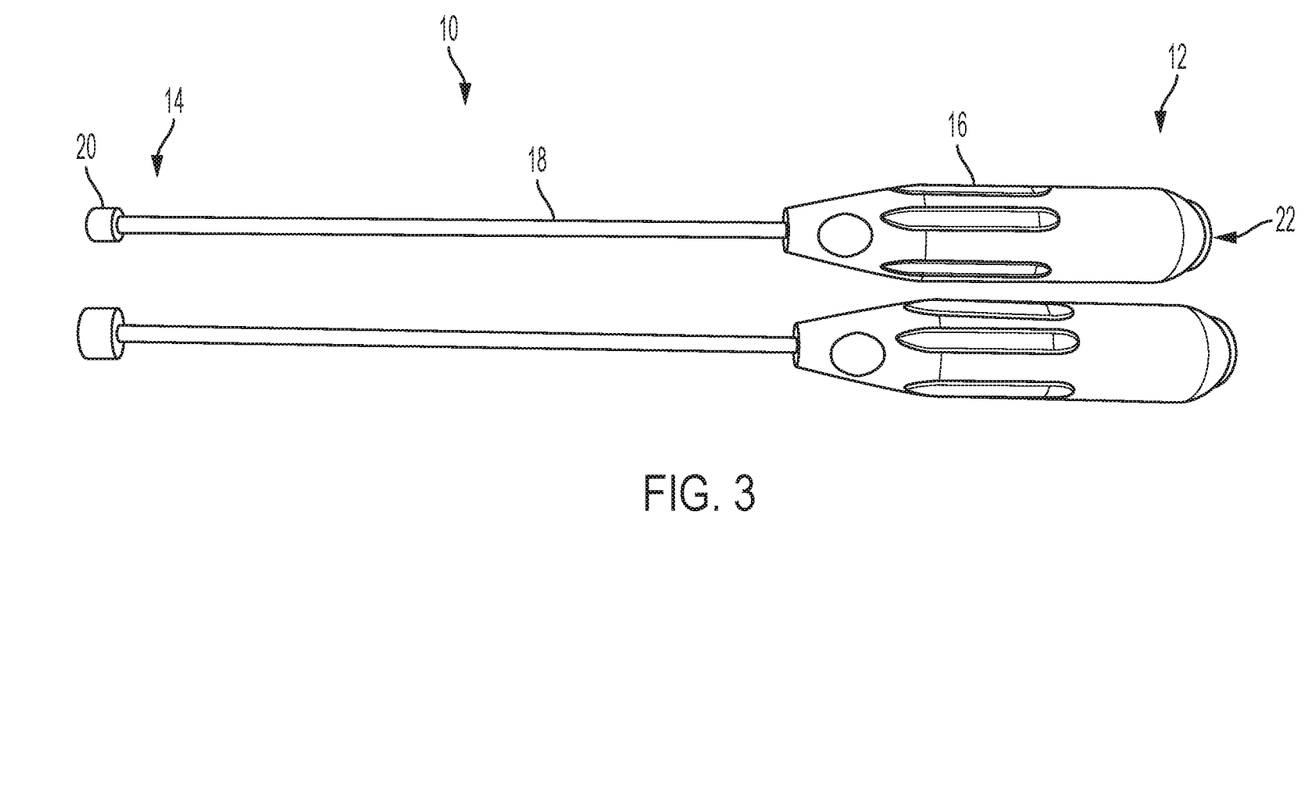
FIG. 3 is a side view schematic representation of a surgical tamp, according to an embodiment.

Referring now to the figures, wherein like reference numerals refer to like parts throughout, FIG. 3 shows a side view schematic representation of a surgical tamp 10, according to an embodiment. The surgical tamp 10 in FIG. 3 comprises a proximal end 12 and a distal end 14. The proximal end 12 of the surgical tamp 10 has a proximal handle 16. The handle 16 can be any suitable shape, with or without ergonomic features, for performing surgical procedures, such as driving a bone dowel allograft into a bone tunnel.

Still referring to FIG. 3, the surgical tamp 10 additionally includes an elongated shaft 18 extending distally from the handle 16. The elongated shaft 18 extends distally to a distal tip 20. The elongated shaft 18 is composed of a flexible material (e.g., rigid stainless steel or reinforced plastic, as not to buckle when impacted). The elongated shaft 18 is cannulated such that there is an inner channel 22 therein extending from the proximal end 12 (through the handle 16) to the distal tip 20. The elongated shaft 18 is flexible (per its composition, as noted above) and cannulated to accommodate various types of guide pins within the inner channel 22. A flexible guide pin (not shown) or a rigid guide pin (not shown) can be inserted into the inner channel 22 through the proximal end 12 of the surgical tamp 10, through the handle 16 and the elongated shaft 18, and out of the distal tip 20. A flexible guide pin can be used for femoral tunnels, while a rigid guide pin can be used for tibial tunnels (flexible and rigid as used in this sentence should be understood by a person of ordinary skill in the art in conjunction with a review of this disclosure). The distal tip 20 can be rounded for impacting the bone dowel allograft or bone chips into the bone tunnel. In the depicted embodiment, the distal tip 20 is cylindrical and opaque.

Figure 4:
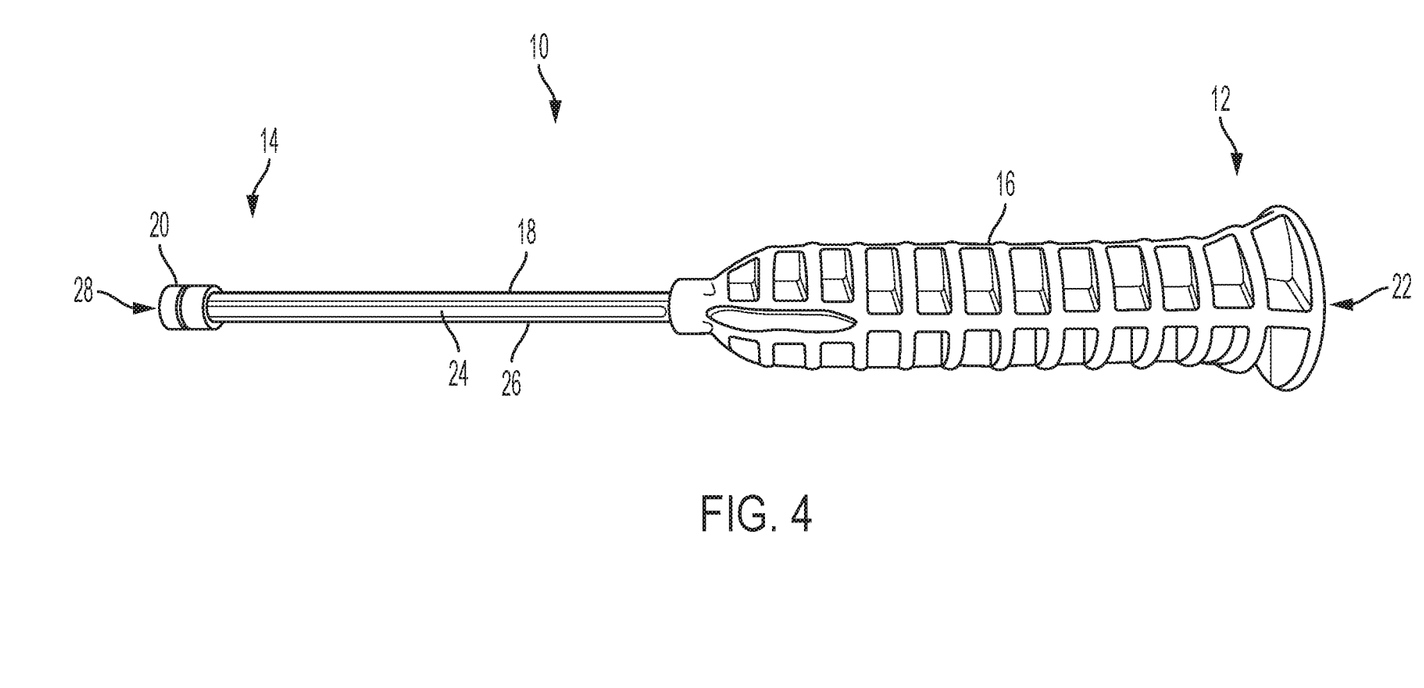
FIG. 4 is a side view schematic representation of a surgical tamp, according to an alternative embodiment.

Turning now to FIG. 4, there is shown a side view schematic representation of the surgical tamp 10, according to an alternative embodiment. In the depicted embodiment, the elongated shaft 18 is composed of a rigid material (e.g., stainless steel or similar material, as should be understood by a person of skill in the art in conjunction with a review of this disclosure). The rigid, elongated shaft 18 comprises a slot 24 extending from the distal tip 20 to the handle 16, as shown in FIG. 4. The slot 24 in the elongated shaft 18 extends into the inner channel 22 of the elongated shaft 18. The slot 24 allows a flexible guide pin (not shown) to exit a side 26 (or exterior surface) of the elongated shaft 18. The ability of the flexible guide pin to exit the side 26 of the shaft 18 allows for axial impaction of the surgical tamp 10 without interference from the guide pin. Due to the slot 24, the movement of the surgical tamp 10 has the ability to change axes while impacting the bone dowel or bone chips into a bone tunnel, such a femoral tunnel.

As also shown in FIG. 4, the distal tip 20 of the surgical tamp 10 is transparent. The transparent, distal tip 20 significantly increases visibility and allows the surgeon to see when the dowel is seated at the distal end 14 of the surgical tamp 10. Specifically, the surgeon can see when the dowel (not shown) is at a distal aperture 28 of the distal tip 20 (wherein the distal aperture 28 is connected to the inner channel 22).

Figure 5:
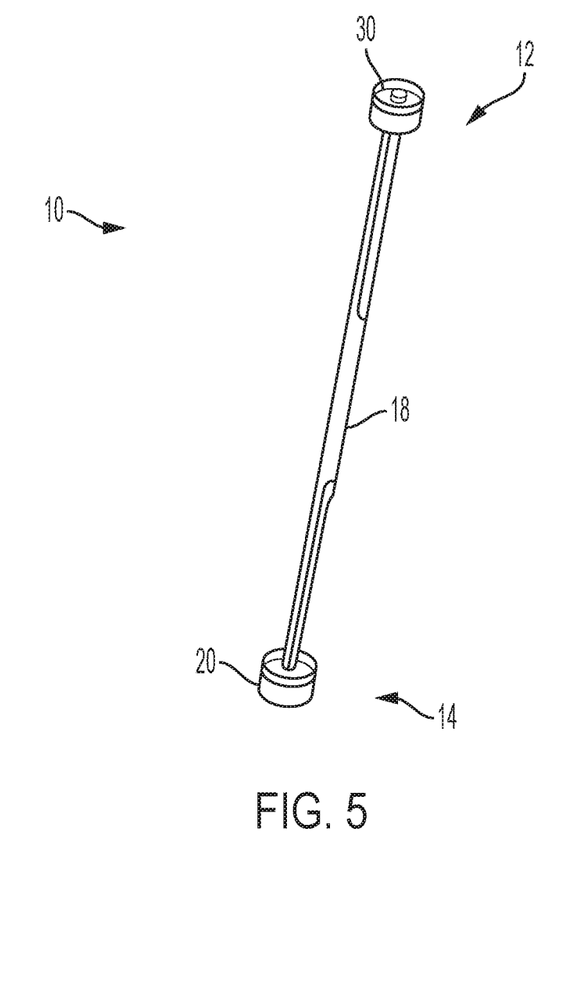
FIG. 5 is a perspective view schematic representation of a surgical tamp, according to another embodiment.
Figure 6:
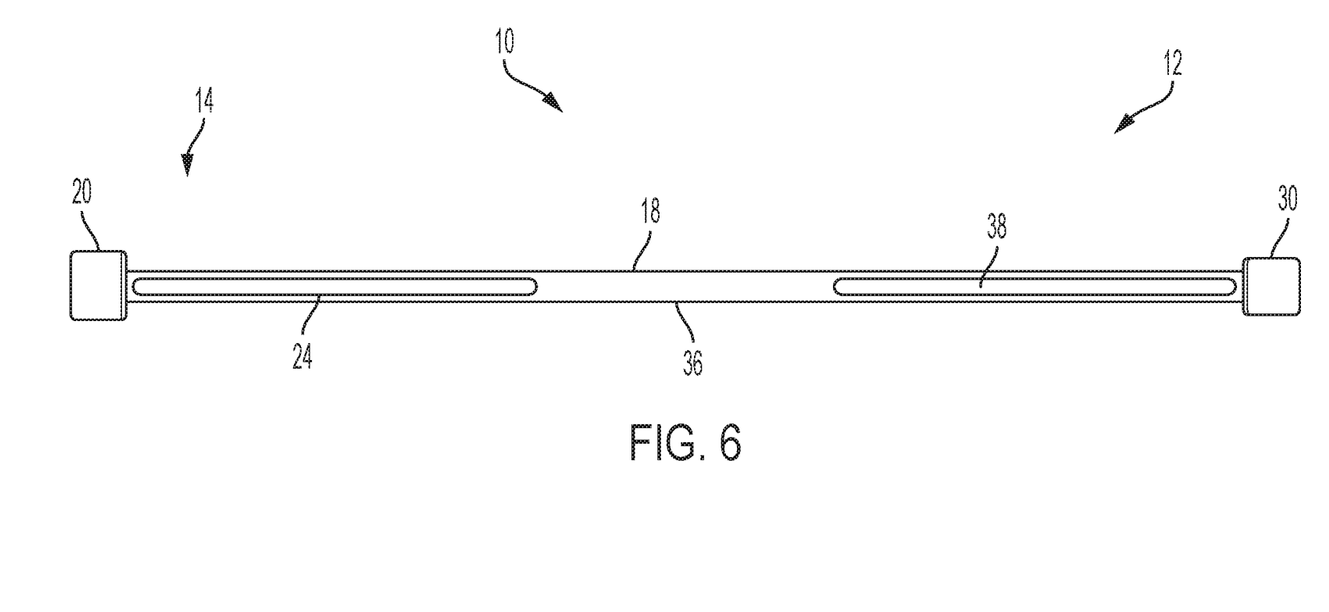
FIG. 6 is a top view schematic representation of the surgical tamp in FIG. 5.
Figure 7:
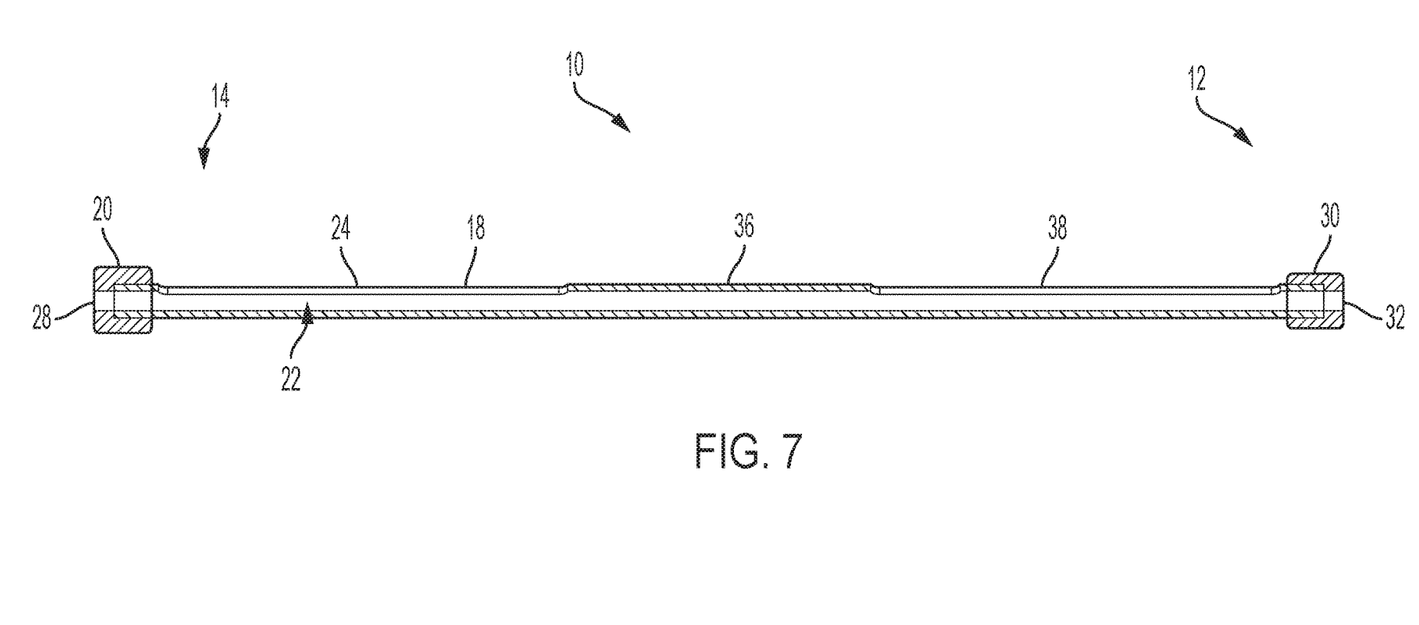
FIG. 7 is a side view schematic representation of the surgical tamp in FIG. 6.

Referring now to FIGS. 5-7, there are shown various views schematic representations of a surgical tamp 10, according to another embodiment. As shown in FIG. 5, the alternative embodiment of the surgical tamp 10 does not include a handle 16 (as shown in FIGS. 3-4). Instead, the surgical tamp 10 has a proximal tip 30 (in addition to the distal tip 20). FIGS. 6 and 7 show that the surgical tamp 10 comprises a cannulated, elongated shaft 18 extending between a distal tip 20 and the proximal tip 30. The distal tip 20 and proximal tip 30 allow for impacting at one or both ends 12, 14 of the surgical tamp 10.

As shown in FIG. 7, the elongated shaft 18 comprises an inner channel 22 extending from the proximal tip 30 to the distal tip 20. In a preferred embodiment, the proximal and distal tips 30, 20 are transparent so that the surgeon can see the dowel at both the proximal and distal ends 12, 14 in the surgical tamp 10. The distal tip 20 comprises the distal aperture 28 extending therethrough and connected to the inner channel 22. The proximal tip 30 also comprises a proximal aperture 32 extending therethrough and connected to the inner channel 22.

As shown in FIG. 6, the elongated shaft 18 additionally comprises a pair of slots, a distal slot 24 extending from a central portion 36 of the elongated shaft 18 toward the distal tip 20 and a proximal slot 38 extending from the central portion 36 of the elongated shaft 18 toward the proximal tip 30. As used herein, the "central portion" can be any portion of the elongated shaft 18 between the distal slot 24 and the proximal slot 38. The distal slot 24 and the proximal slot 38 both accommodate and allow for a flexible guide pin (not shown). As described above, slots 24, 38 in the elongated shaft 18 allow for the movement of the surgical tamp 10 to change axes while impacting bone dowels and bone chips. Again, the ability of the flexible guide pin to exit the side 26 of the shaft 18 allows for axial impaction of the surgical tamp 10 without interference from the guide pin.

Figure 8:
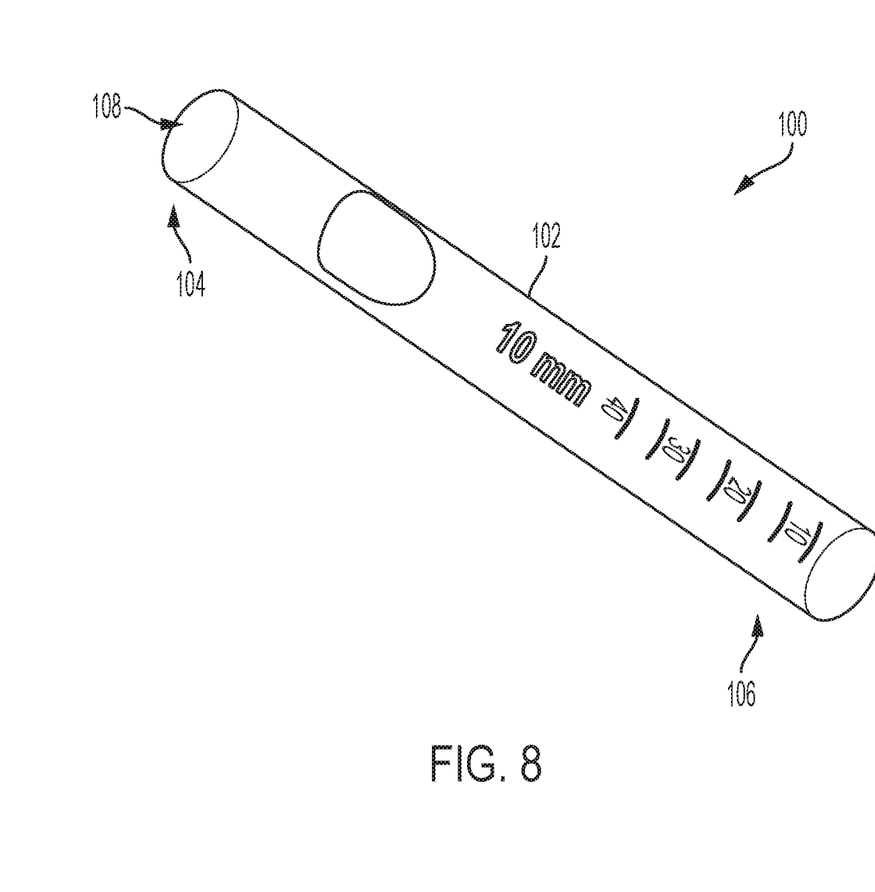
FIG. 8 is a perspective view schematic representation of a delivery tube, according to an embodiment.
Figure 9:
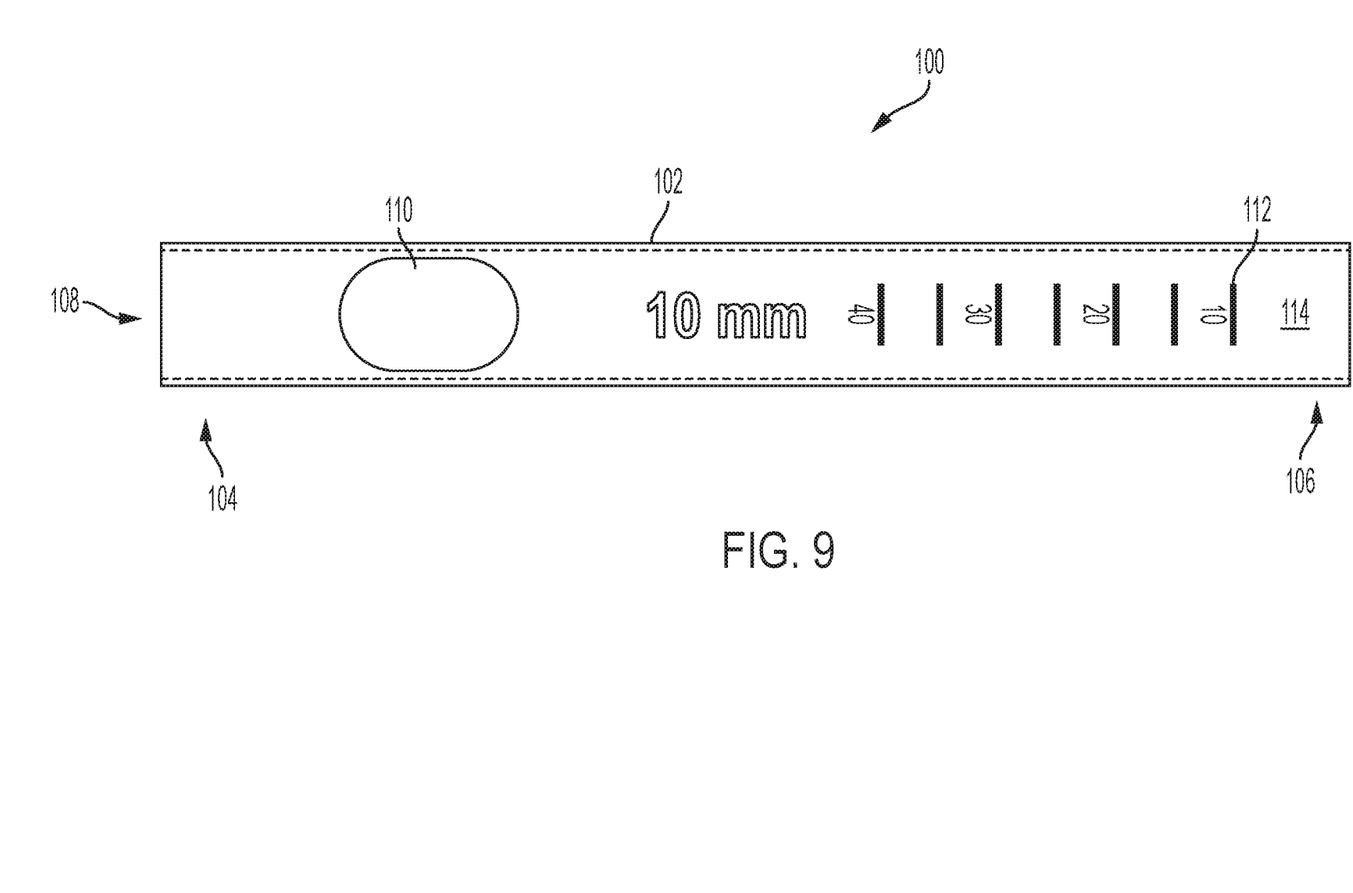
FIG. 9 is a top view schematic representation of the delivery tube of FIG. 8.
Figure 10:
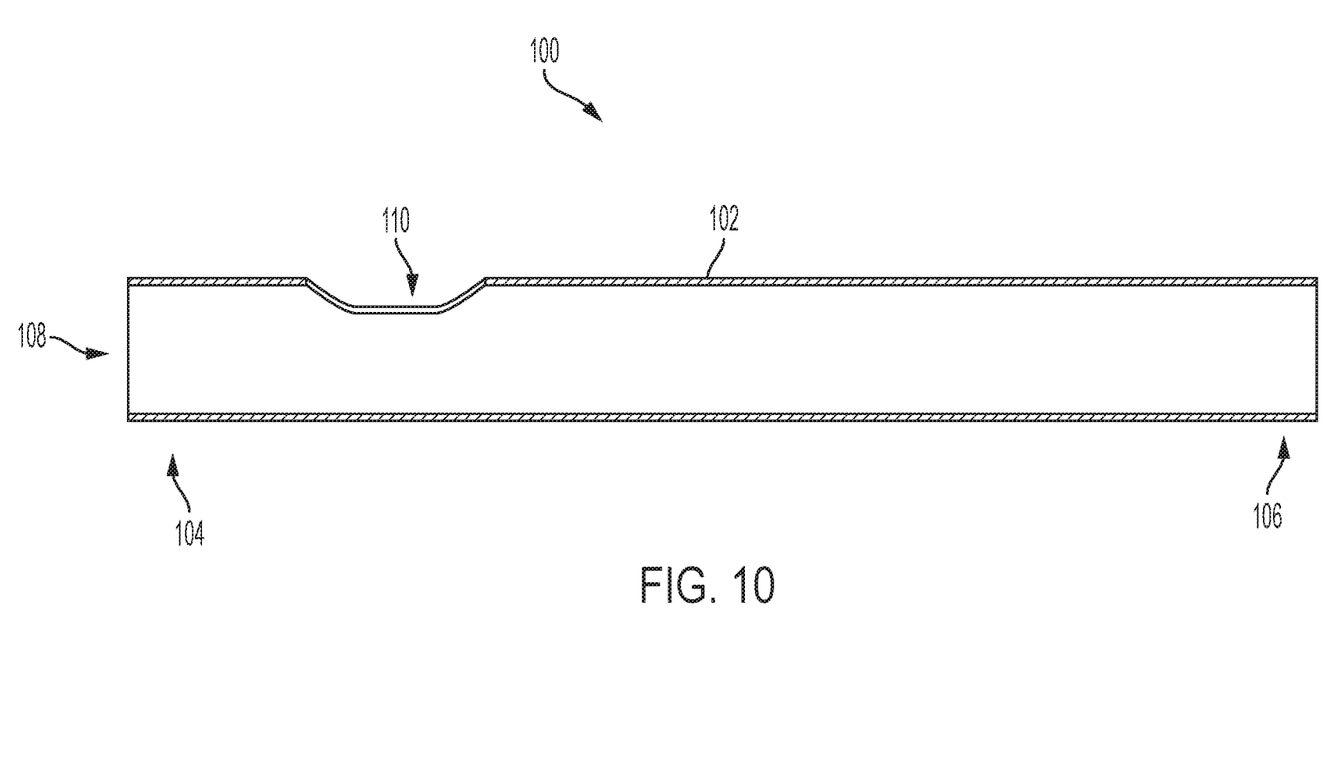
FIG. 10 is a side view schematic representation of the delivery tube of FIG. 9.

Turning now to FIGS. 8-10, there are shown various views schematic representations of a delivery tube 100, according to an embodiment. The delivery tube 100, such as that shown in FIG. 8, is used in conjunction with the surgical tamp 10 (in any embodiments shown in FIGS. 3-7) for inserting bone dowel allografts (not shown) into the joint or for delivering bone chips (not shown) directly into the bone tunnels. Bone dowel allografts are generally composed of course, cancellous bone. The rough texture of the bone dowels makes it extremely difficult to pass the surrounding soft tissue at the surgical site and into the joint. The delivery tube 100 aids in the insertion of the bone dowel by providing a smooth path into the joint and protecting the surrounding soft tissue. As for bone chips, the delivery tube 100 provides a vessel to carry the chips through the joint, directly into the bone tunnel so that a single bone chip does not fall into an undesired location.

As shown in FIG. 8, the delivery tube 100 is preferably transparent so that the surgeon can see the bone dowel (not shown) or bone chips (not shown) therein. In an embodiment, the delivery tube 100 is machined from one piece of material. Preferably, the delivery tube 100 is composed of a smooth, hard plastic material (e.g., a thermoplastic polymer such as PETG). FIGS. 9-10 show that the delivery tube 100 comprises an elongated shaft 102 with an open, proximal end 104 and an open, distal end 106. The elongated shaft 102 has an inner channel 108 extending from the proximal end 104 to the distal end 106. In use, a bone dowel or bone chips are within the inner channel 108 of the delivery tube 100 and a surgical tamp 10, such as that shown in FIGS. 5-7, is inserted into the open, proximal end 104 of the delivery tube 100 to impact the bone dowel or bone chips in the distal direction within the inner channel 108.

Still referring to FIGS. 9-10, the delivery tube 100 includes an aperture 110 (or window) extending through the delivery tube 100 into the inner channel 108. In the depicted embodiment, the aperture 110 is near the proximal end 104 of the elongated shaft 102. The aperture 110 allows for loading additional bone chips (not shown) into the inner channel 108 of the delivery tube 100 without removing the delivery tube 100 from the joint.

In the embodiment of the delivery tube 100 shown in FIGS. 8 and 9, the delivery tube 100 comprises one or more indicators 112 along its exterior surface 114. The indicators 112 provide a reference for depth. In the depicted embodiment, the indicators 112 are measurements in 10 mm increments, although any suitable system for measuring depth can be used. As the bone chips are inserted into the inner channel 108 of the delivery tube 100 (e.g., through the aperture 110), a surgeon can gauge how much of the bone tunnel will be filled by bone chips.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A surgical impacting system, comprising:
    a surgical tamp having a proximal end and a distal end with an elongated shaft including a central portion extending therebetween;
    a handle positioned at the proximal end and a distal tip positioned at the distal end;
    an inner channel extending through the elongated shaft from the proximal end to the distal end;
    a first slot formed through an exterior surface of the elongated shaft and into the inner channel and extending from the distal tip to a position distal to a distal end of the handle; and
    wherein the first slot is configured and structured to accommodate a guide pin therein.

2. The system of claim 1, wherein the distal tip is transparent.

3. The system of claim 1, wherein the distal tip comprises a distal aperture connected to the inner channel.

4. The system of claim 1, wherein the distal tip is rounded.

5. The system of claim 1, further comprising a delivery tube having an open, proximal end and an open, distal end with an inner channel extending therebetween, wherein the surgical tamp is movable within the inner channel of the delivery tube.

6. The system of claim 1, wherein the distal tip is cylindrically shaped.

7. The system of claim 1, wherein the distal tip comprises a larger diameter than a diameter of the elongated shaft.

* * * * *